United States Patent [19]

Gabridge

[11] 4,435,508
[45] Mar. 6, 1984

[54] TISSUE CULTURE VESSEL

[76] Inventor: Michael G. Gabridge, Trudeau Rd., Saranac Lake, N.Y. 12983

[21] Appl. No.: 323,653

[22] Filed: Nov. 20, 1981

[51] Int. Cl.³ .............................................. C12M 3/00
[52] U.S. Cl. .................... 435/284; 435/285; 435/298; 435/299; 422/102; 210/445
[58] Field of Search .............. 435/284, 285, 298, 299, 435/809; 422/102; 210/445

[56] References Cited

U.S. PATENT DOCUMENTS

| | | | |
|---|---|---|---|
| Re. 30,351 | 7/1980 | Hoehn et al. | 55/16 |
| 2,966,235 | 12/1960 | Kammermeyer | 55/16 |
| 3,651,618 | 3/1972 | Klein et al. | 55/16 |
| 4,195,131 | 3/1980 | Papas | 435/316 |
| 4,301,252 | 11/1981 | Baker et al. | 435/809 |

*Primary Examiner*—Ferris H. Lander
*Attorney, Agent, or Firm*—Marla J. Church

[57] ABSTRACT

The tissue culture vessel of this invention comprises two rigid plates with aligned apertures. The upper plate is separated from the lower plate by a rubber gasket and an interchangeable growth substrate. The two plates are held together with screws. Materials used are nontoxic autoclavable and reusable. Access to the vessel is provided through a petri dish cover placed in a circular channel in the top surface of the upper plate. Such access allows for physical manipulation of the materials contained within the vessel while maintaining aseptic conditions.

5 Claims, 3 Drawing Figures

TISSUE CULTURE VESSEL

BACKGROUND OF INVENTION

This invention relates to a tissue culture vessel that provides easy access to cells and variability of growth substrate for microscopic examinations at high magnifications.

A current problem in tissue technology is the unavailability of a vessel for the in vitro cultivation of cells and explants that allows for high resolution microscopy along with easy accessibility to the materials contained within the vessel. A wide variety of devices presently on the market have been used with considerable success but each has limitations which restrict usefulness and limit versatility.

Generally, the various devices of the prior art are of two types of construction. For example, the first type allows for growth and easy access to the culture sample, but the materials used do not permit high magnification microscopy. These include such growth containers as glass and plastic bottles, flasks and petri dishes that have thick and/or irregular surfaces which distort the image when viewed at high magnifications. Often, stress lines, bubbles and scratches interfere with the visual morphological assessments. In addition, phase and interference microscopy are far from optimal because of the thickness of the growth surface. These devices also fail to offer any variability in the nature of the growth substrate.

The second type incorporates thin glass or plastic coverslips as the growth substrate sandwiched between metal plates. The coverslips are separated by a ring-like gasket or are permanently cemented to one of the plates. Access to this type of chamber is either with a syringe needle or by a tube projecting radially from the enclosed area. For example, U.S. Pat. No. 2,942,520 discloses a tissue culture device of this type where any physical manipulation of the cellular material inside the device requires complete disassembly. Maintenance of a sterile environment during disassembly is difficult if not impossible. Such devices permit the exchange of liquid or media contained within, but do not provide access to the cellular material located on the growth surface.

SUMMARY OF INVENTION

The invention described herein solves the above-mentioned problems inherent in prior art devices. The tissue culture vessel of this invention permits ready sterile access to perform manipulative operations on tissue cultures growing therein. The vessel is made of several components including a rigid upper and base plate of autoclavable, nontoxic material, a sealing gasket, an interchangeable growth substrate and a cover. In the assembled vessel, the plates have mutually aligned apertures that are concentric with an axis passing through the geometric center of the top and bottom surface of the plates. The top surface of the upperplate has a circular channel concentric with the aperture, but removed from a contacting relationship with the aperture by the material of the upper plate. The bottom surface of the upper plate has a groove concentric with and open to the aperture. The bottom surface of the base plate has an inset concentric with and open to the aperture to accommodate a microscope objective.

When assembled, the interchangeable growth substrate is situated between the top surface of the base plate and bottom surface of the top plate and covers the aperture in the base plate. The gasket fits into the groove in the bottom surface of the upper plate and forms a seal between the interchangeable growth substrate and the upper plate. The cover is placed into the circular channel to cover the aperture in the upper plate.

Suitable growth substrates include glass or plastic coverslips and a variety of flexible materials ranging from transparent and gas-permeable Teflon to polyester sheeting and titanium. The use of thin, flexible films is an important asset of this invention for electron microscopy studies, since thin sections can be cut directly through the cells, substrate and the embedding medium.

The ready access to the interior of the vessel facilitates studies where instruments must be employed, as in micromanipulation work, and also allows explant cultures to be moved or added to the growth vessel. In addition, cell cloning studies can be performed in the tissue culture vessel since it combines excellent resolution at high magnification while permitting the entry of micropipettes and instruments.

Versatility of this invention is evidenced further in the possible coverings for the vessel. A perfusion cover is readily constructed to accommodate inlet and outlet tubes for gas and/or liquid perfusion. Perfusion is a widely used technique and adapts easily to the tissue culture vessel. Covers could also be modified to hold pH electrodes, oxygen electrodes, or related instrumentation.

DETAILED DESCRIPTION OF THE DRAWINGS

Figure 1:
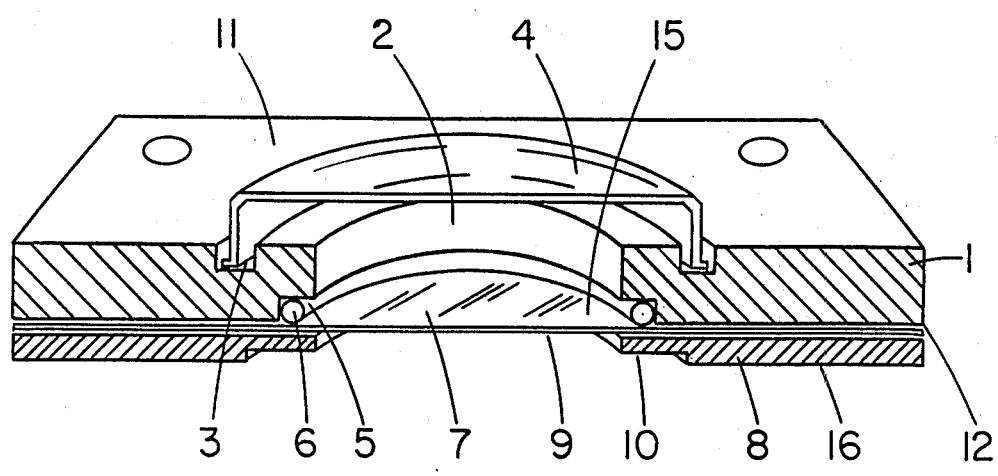
FIG. 1 is a schematic drawing in perspective cross-section of the tissue culture vessel.

With reference to the drawings, particularly FIG. 1, upper plate 1 of the tissue culture vessel is constructed from a block of Teflon or other rigid nontoxic material, the most convenient size for microscopy is $2'' \times 3'' \times \frac{1}{4}''$. Aperture 2 is formed in the geometric center of the area of top surface 11 of upper plate 1 and provides access to concentric well 15 wherein the culture is grown. Circular channel 3, concentric with aperture 2 on top surface 11 of upper plate 1, is displaced from aperture 2 by the material of upper plate 1, and provides a recess for a suitable cover 4, such as a petri dish cover. Channel 3 also prevents the entry of contaminants into well 15. Groove 5 concentric with and open to aperture 2 and recessed below bottom surface 12 of upper plate 1 holds rubber gasket 6 that provides a seal between upper plate 1 and growth surface 7. Growth surface 7 can be a glass or plastic coverslip, a sheet of gas-permeable membrane or any other non-toxic material that will support the growth of cells. Growth substrates tested included No. 1 glass coverslips, gas-permeable membranes in sheet form, transparent silicone rubber sheets, Teflon films and coverslips coated with collagen. The flexible growth substrates were gently stretched while securing base plate 8 to upper plate 1 in order to prevent wrinkling. Each of the above-referenced substrates supported the growth of lung fibroblasts with the retention of normal morphological characteristics when examined after 72 hours in culture. The individual cells in monolayer format were examined at high magnifications (250–400×). The yields of cells grown in the tissue culture vessel were the same as those in standard petri dishes.

Figure 2:
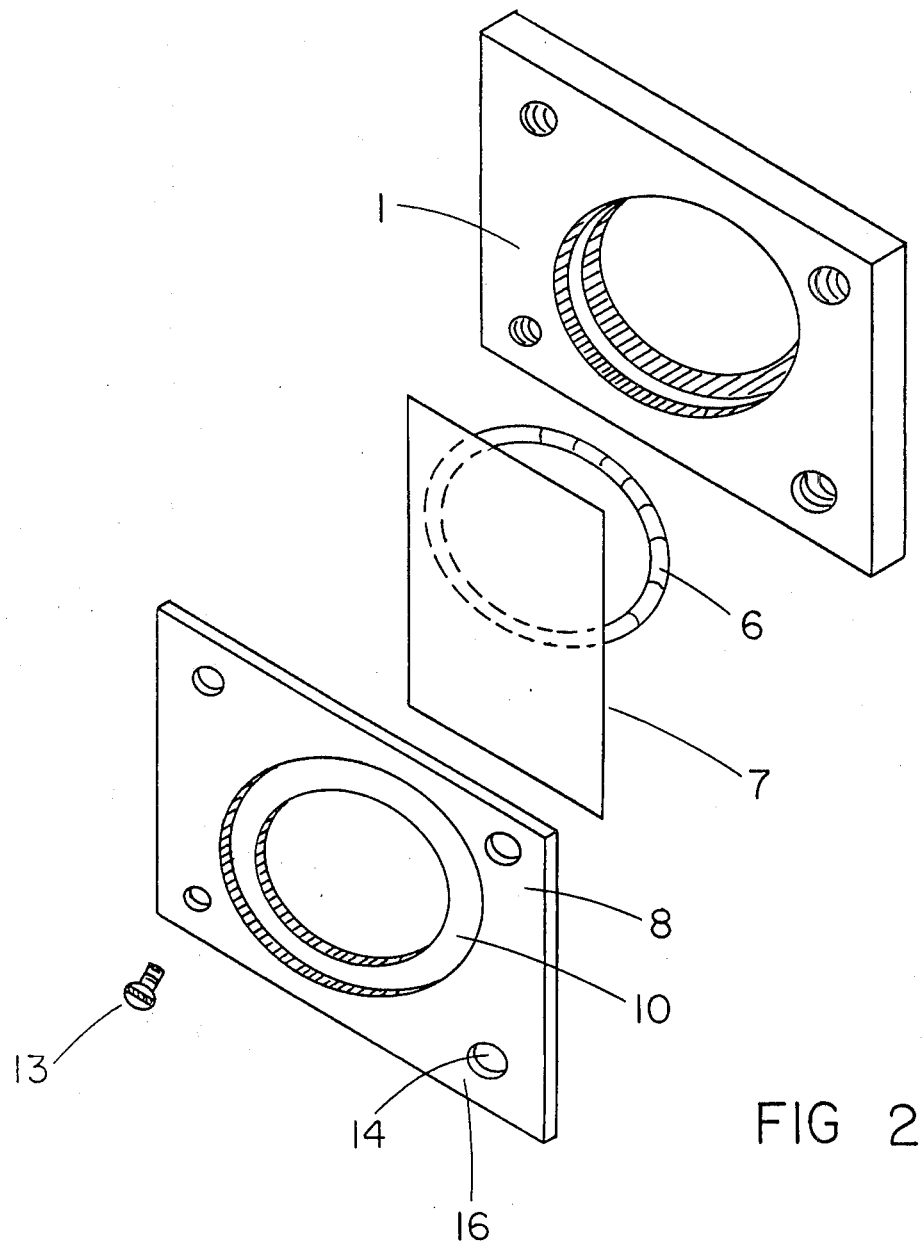
FIG. 2 is a perspective view of the culture vessel of FIG. 1 showing the component parts.

Base plate 8 is constructed most conveniently from an aluminum sheet (1/16" thick) with dimensions that correspond to the dimensions of upper plate 1. Base plate 8 can also be made with stainless steel or any other similar firm, inert material. Central aperture 9 cut in base plate 8 aligns with aperture 2 through upper plate 1. Inset 10 concentric with and open to aperture 9 provides access for a microscope objective to permit viewing of the entire underside of growth surface 7. As shown in FIG. 2, base plate 8 is secured to upper plate 1 with a plurality of screws 13 which are threadably engaged in screwholes 14. Screwholes 14 in base plate 8 are contersunk, such that the bottom surface 16 of base plate 8 is completely flat after final assembly.

Figure 3:
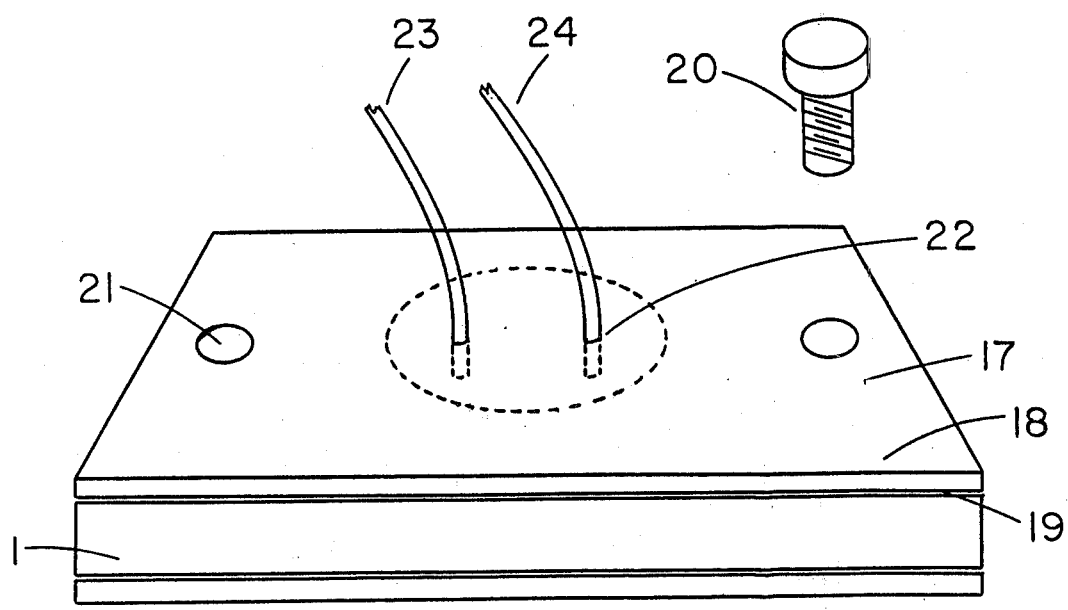
FIG. 3 is a perspective view of the vessel with the alternate perfusion cover.

FIG. 3 shows alternate perfusion cover 17 for the tissue culture vessel. It is made out of polycarbonate or any other rigid, inert autoclavable plastic that permits the vessel to be used as a perfusion chamber. Perfusion cover 17 is made to correspond to the size of the culture vessel, usually 2"×3"×3/16". Perfusion cover 17 has top 18 and bottom 19 substantially parallel major surfaces. Thumb screws 20, threadably engaged in screwholes 21, secure perfusion cover 17 to upper plate 1 of the tissue culture vessel. A seal is maintained between perfusion cover 17 and upper plate 1 by placing gum rubber sheeting between bottom surface 19 of perfusion cover 17 and top surface 11 of upper plate 1. Perfusion ports 22 situate on either side of the geometric center of top surface 18 communicate with upper plate aperture 2 (FIG. 1) and allow for insertion of inlet 23 and outlet tube 24. Tubes 23 and 24 are made of auoclavable plastic and held in place with autoclavable cement.

The assembled tissue culture vessel includes upper plate 1, rubber gasket 6, growth surface 7 and base plate 8. This assembly, with screws 13 in place but not completely tightened, can be placed in an enclosed container or wrapped and autoclaved. After cooling, screws 13 are tightened and sterile cover 4 is added. For convenience, the culture vessel can be stored in square, plastic petri dishes. For use, each chamber is inoculated with the appropriate media and cell sample.

While the invention has been particularly shown and described with reference to several preferred embodiments thereof, it will be understood by those skilled in the art that various changes in form and detail may be made therein without departing from the true spirit and scope of the invention as defined by the appended claims.

I claim:

1. A tissue culture vessel for the growth of cellular material comprising:
   a. a rigid upper plate of autoclavable, nontoxic material having a first aperture therethrough, a circular channel concentric with and remote from the first aperture and being accessible from the top surface of the upper plate, and a groove concentric with and adjacent to the first aperture and accessible from the bottom surface of the upper plate;
   b. a rigid base plate of autoclavable material affixed to the upper plate and having a second aperture therethrough being substantially mutually aligned with the first aperture, the bottom surface of the base plate having an inset concentric with the second aperture and being accessible from the bottom surface of the base plate;
   c. an interchangeable nontoxic growth substrate situated between the bottom surface of the upper plate and the top surface of the bottom plate and extending at least across the second aperture, providing an optically nondistorting surface for the use of high magnification microscopy visualization of the cellular material contained therein;
   d. a nontoxic gasket located in the groove and in an abutting relationship with the interchangeable growth substrate and the upper plate; and
   e. a removeable cover situated in the circular channel and extending over and enclosing the first aperture.

2. The tissue culture vessel of claim 1 wherein the cover is a petri dish cover.

3. The tissue culture vessel of claim 1 wherein the interchangeable growth substrate comprises a No. 1 glass coverslip.

4. The tissue culture vessel of claim 1 wherein the interchangeable growth substrate comprises gas-permeable membranes in sheet form, transparent silicone rubber sheets, and Teflon films.

5. The tissue culture vessel of claim 1 wherein the cover is a perfusion cover made out of a rigid, inert autoclavable plastic containing perfusion ports that provide for insertion of inlet and outlet tubes.

* * * * *